US010820905B2

(12) United States Patent
Haller et al.

(10) Patent No.: US 10,820,905 B2
(45) Date of Patent: Nov. 3, 2020

(54) TISSUE LIGATION APPARATUS WITH A ROTATING SPOOL ASSEMBLY AND A VALVE ASSEMBLY

(71) Applicant: Intelligent Endoscopy LLC

(72) Inventors: Fritz Haller, Clemmons, NC (US); Melissa Clark, Clemmons, NC (US); Eugene Skelton, Dublin (IE); Anthony Wright, Clemmons, NC (US); Darren Corner, Clemmons, NC (US)

(73) Assignee: Intelligent Endoscopy LLC, Clemmons, NC (US)

( * ) Notice: Subject to any disclaimer, the term of this patent is extended or adjusted under 35 U.S.C. 154(b) by 435 days.

(21) Appl. No.: 15/527,830

(22) PCT Filed: Nov. 24, 2015

(86) PCT No.: PCT/US2015/062462
§ 371 (c)(1),
(2) Date: May 18, 2017

(87) PCT Pub. No.: WO2016/086003
PCT Pub. Date: Jun. 2, 2016

(65) Prior Publication Data
US 2017/0303930 A1 Oct. 26, 2017

(51) Int. Cl.
*A61B 17/12* (2006.01)
*A61B 17/00* (2006.01)
(52) U.S. Cl.
CPC ............ *A61B 17/12013* (2013.01); *A61B 2017/00296* (2013.01); *A61B 2017/12018* (2013.01)
(58) Field of Classification Search
CPC ........... A61B 2017/12018; A61B 2017/00296; A61B 1/00087; A61B 1/00089;
(Continued)

(56) References Cited

U.S. PATENT DOCUMENTS 5,385,568 A * 1/1995 Boebel ............... A61B 17/0482
606/144
5,398,844 A * 3/1995 Zaslavsky ........ A61B 17/12013
221/208
(Continued)

FOREIGN PATENT DOCUMENTS

WO 2016/086003 A1 6/2016

OTHER PUBLICATIONS

International Search Report and Written Opinion for Application No. PCT/US2015/062462, dated Feb. 4, 2016.

*Primary Examiner* — Kathleen S Holwerda
*Assistant Examiner* — Kankindi Rwego
(74) *Attorney, Agent, or Firm* — Mintz Levin Cohn Ferris Glovsky and Popeo, P.C.

(57) ABSTRACT

Provided herein is a mechanical device including a rotating spool assembly and a disposable valve assembly. The rotating spool assembly includes a hub, an arm, and a spool inserted through an opening in the arm. The rotating spool assembly can be sterilized after each use. The disposable valve assembly includes a mating stem member, a sealing member, and a flushing port member. The disposable valve assembly can be disposed of after every use. A loading member is also provided including a wire that can be formed from metal drawn out into a thin flexible thread. The loading member can be pre-formed in a helix to form coils in the wire. A release cord is provided including a braided cord with two single filaments and a plurality of beads formed along a length of the single filaments at a distal end of the braided cord.

24 Claims, 13 Drawing Sheets

(58) Field of Classification Search
CPC ............ A61B 1/00091; A61B 1/00094; A61B 1/00096; A61B 1/00098; A61B 1/00101; A61B 1/00112; A61B 1/0014; A61B 17/00234; A61B 17/12; A61B 17/12009; A61B 17/12013; A61B 2017/00292; A61B 2017/12004; A61B 1/00131
USPC ....................................................... 606/139
See application file for complete search history.

(56) References Cited

U.S. PATENT DOCUMENTS

| | | | |
|---|---|---|---|
| 5,624,453 A | | 4/1997 | Ahmed |
| 5,695,491 A | * | 12/1997 | Silverstein ......... A61B 1/00133 600/104 |
| 6,007,551 A | | 12/1999 | Peifer et al. |
| 6,315,782 B1 | | 11/2001 | Chu et al. |
| 6,676,672 B2 | * | 1/2004 | Chu ................. A61B 17/12013 606/139 |
| 6,685,713 B1 | | 2/2004 | Ahmed |
| 2002/0002361 A1 | * | 1/2002 | Fanelli ............... A61B 17/3415 604/516 |
| 2004/0006256 A1 | | 1/2004 | Suzuki et al. |
| 2006/0212042 A1 | * | 9/2006 | Lamport ............. A61B 17/221 606/108 |
| 2008/0255412 A1 | | 10/2008 | Surti |
| 2009/0131748 A1 | | 5/2009 | Chami |
| 2014/0081294 A1 | | 3/2014 | Kamler |
| 2014/0100581 A1 | * | 4/2014 | Reimels ............ A61B 17/8858 606/99 |

* cited by examiner

TISSUE LIGATION APPARATUS WITH A ROTATING SPOOL ASSEMBLY AND A VALVE ASSEMBLY

RELATED APPLICATIONS

This application is a national stage application, filed under 35 U.S.C. § 371, of PCT International Patent Application No. PCT/US2015/062462, filed on Nov. 24, 2015, and claims benefit of priority to U.S. Provisional Patent Application No. 62/085,272, filed on Nov. 27, 2014, both of which, including their contents, are incorporated herein by reference in their entireties.

FIELD

The present disclosure relates generally to tissue ligation.

BACKGROUND

Swollen and enlarged veins in the esophagus are commonly called esophageal varices. Esophageal varices have the potential to rupture and cause excessive bleeding in the esophagus, which can cause death in certain circumstances. Ligation of the varices can be performed to treat bleeding varices. Ligation can also be performed as a preventative measure to strangulate and remove the varices before they reach a stage where bleeding is a distinct risk. For ligation to be successfully performed through common practice, the varices must be pulled into a hollow chamber through suction, whereby elastic ligation bands are released over the tissue to strangulate it. Strangulation leads to death of the tissue and the subsequent natural detachment of the varices.

Endoscopic hemorrhoid band ligation (HBL), similar in technique to the variceal banding described above is an important advancement in the treatment of symptomatic internal hemorrhoids (IH). Multiple rubber bands can be applied in one session, and further bands can be applied in subsequent sessions if a single session fails to completely eradicate the internal hemorrhoids. The treatment success rate is high, while the long-term recurrence rate is low. Symptomatic hemorrhoids in adults is considered one of the most prevalent anorectal disorders. Hemorrhoids of different grades can be found in more than 80%-90% of patients undergoing sigmoidoscopy or colonoscopy. Hemorrhoids are either internal or external depending on the localization above or below the dentate line.

A new successful technique for the treatment of high grade dysplasia is endoscopic mucosal resection. This involves the piece-meal endoscopic resection of early neoplastic lesions larger than 15-20 mm. Before using band ligation, this was a laborious procedure. Multiband mucosectomy is a new safe and very effective technique using a modified variceal band ligator. Sub-mucosal lifting and pre-looping of the snare in the cap is not necessary and multiple resections can be performed with a single snare. The ligator suctions the targeted tissue into pseudo polyps and then the snare removes them in succession.

For all three situations mentioned above, the ligation is performed in conjunction with an endoscope or other device that can be used to allow deep access to the human digestive tract. Endoscopes generally consist of a rigid or flexible tube with a working channel of varying internal diameters to allow a variety of medical instruments to be deployed and used in the human digestive tract. Endoscopes also feature a camera on the distal tip of the flexible tube to allow direct visualization of the digestive tract as well as light, suction and fluid delivery systems.

Devices that facilitate this functionality are commonly called multi-band ligation devices. These devices consist of a hollow cylindrical barrel component which fits on the distal end of the endoscope, and that is configured to apply multiple bands over tissue suctioned into the device. There are many examples of multi-band ligation devices currently in use today. As well as this, a variety of instruments for effecting the ligation of body tissue by the application of an elastic band are known in the art in the form of single ligation band devices.

SUMMARY

Various methods and devices are provided for performing band ligation. In one aspect, an endoscopic surgical device has a rotating spool assembly and a valve assembly. The rotating spool assembly has a hub, an arm contiguous with the hub, and a rotating spool inserted through the arm. The hub has an opening formed therein. The valve assembly has a mating stem member, a sealing member, and a flushing port member. The mating stem member has a lumen extending through a longitudinal center thereof and has the sealing member extending thereacross. The lumen is aligned on a proximal end of the mating stem member with the opening in the rotating spool assembly. The valve assembly is coupled to a distal end of the rotating spool assembly.

The endoscopic surgical device can vary in a variety of ways. For example, the rotating spool assembly can include a substantially hook-shaped member that rotates as one with the spool, the substantially hook-shaped member being configured to receive a cable. As another example, the spool can comprise a tapered toothed groove sized to grip a release cord. In another example, the spool can include first and second posts protruding from a surface thereof and positioned next to one another. The first and second posts can be configured to receive a cable therearound. In another embodiment, the spool can comprise at least one post protruding from a surface thereof and a groove in the surface positioned proximally from the post. As another example, the mating stem member can include an upper body with one or more tabs formed on the upper body. The mating stem member can also include a tapered section at a distal end thereof, and the tapered section can be shaped to be inserted into an auxiliary port of an endoscope to form a surface-to-surface mating engagement with a corresponding internal geometry of the auxiliary port. As another example, the rotating spool assembly can couple to the valve assembly using a quarter turn bayonet fitting.

In another aspect, an endoscopic surgical device is provided that has a spool assembly and a loading wire. The spool assembly has a rotating member and a stem having a lumen extending therethrough. The loading wire extends through the lumen in the stem of the spool assembly. The loading wire also has a proximal end extending proximally from the lumen in the stem toward and has a distal end extending distally from the lumen in the stem. The distal end of the loading wire has a hook formed thereon and is configured to couple to a thread such that the proximal end of the loading wire can be pulled proximally to pull the thread through the spool assembly.

The endoscopic surgical device can be varied in a variety of ways. For example, the loading wire can be formed from metal drawn out into a thin flexible thread. As another example, the loading wire can form one or more coils. The coils can constrain the wire in a coiled configuration in a first position when the wire is separated from the spool assembly, and the wire can conform to a longitudinal shape of the lumen in a second position when the wire is disposed through the lumen. In another embodiment, the proximal end of the loading wire includes a hook formed thereon. In another example, the hooks can be formed from the wire being turned back upon itself to form a hook shape, and a central axis of a distal end of each hook can be co-linear with a central axis of the wire. The loading member can also be formed from a braiding of two or more single wires. As another example, the loading member can be formed from a polymer. A central segment of the wire can also form one or more coils, and proximal and distal portions of the wire can be formed of straight sections.

In another aspect, a release cord is provided with a braided cord and a plurality of beads. The braided cord has first and second single filaments. The single filaments are braided together at a proximal end of the braided cord and separated at a distal end of the braided cord. The plurality of beads are formed along a length of each of the first and second single filaments at the distal end of the braided cord. The plurality of beads are positioned such that no two beads are at a same distance from the proximal end of the braided cord.

The release cord can be varied in a variety of ways. For example, the beads can be substantially spherical. The beads can also be made of a polymer. In another example, a proximal section of the release cord can be formed into a closed loop configuration, and the closed looped configuration can be sized to fit through a working channel of an endoscope. In another example, the closed looped configuration at the proximal end can be created by attaching a separate closed loop shaped component through mechanical means.

In another aspect, a system for tissue ligation is provided with a rotating spool assembly, a valve assembly, a wire, and a release cord. The rotating spool assembly has a hub and a spool, with an opening being formed in the hub. The valve assembly has a mating stem member. A lumen extends through a longitudinal center of the mating stem member and aligns on a proximal end of the mating stem member with the opening in the rotating spool assembly. The valve assembly is coupled to a distal end of the rotating spool assembly. The wire has a cross sectional dimension that does not exceed the lumen of the valve assembly, and hooks are formed on each end of the wire. The release cord has a braided cord with first and second single filaments. The single filaments are braided together at a proximal end of the braided cord and separated at a distal end of the braided cord. A plurality of beads are formed along a length of each of the first and second single filaments at the distal end of the braided cord.

The system can vary in any number of ways. For example, the plurality of beads can be positioned such that no two beads are at a same distance from the proximal end of the braided cord. As another example, the spool can have a substantially hook-shaped member on a surface thereof, and a proximal end of the release cord can be attached to the substantially hook-shaped member.

As another aspect, a method for assisting with tissue ligation is provided. The method includes passing a loading member having a wire with a hook formed on at least a distal end through an opening in a rotating spool assembly having a spool, distally along a lumen formed in a valve assembly coupled to the rotating spool assembly, and distally along a length of a working channel of an endoscope such that the hook protrudes from a distal end of the working channel. The method also includes securing a proximal end of a release cord onto the hook. The release cord has a braided cord with at least two single filaments, and the single filaments are separated at a distal end of the braided cord and having a plurality of beads formed along a distal length of each of the single filaments. The method additionally includes drawing the proximal end of the release cord proximally through the working channel, the valve assembly, and the rotating spool assembly until the proximal end of the release cord protrudes from a proximal end of the rotating spool assembly. The method further includes attaching the proximal end of the release cord to the spool of the rotating spool assembly.

The method can vary in any number of ways. For example, the plurality of beads on the single filaments of the release cord can be positioned such that no two beads are at a same distance from the proximal end of the braided cord. The method can also further include wrapping a plurality of ligation bands around an outside distal surface of the endoscope, with each ligation band being positioned in front of corresponding sets of beads on each of the single filaments. As another example, the method can include positioning a distal end of the endoscope against a tissue to be ligated, and retracting the release cord proximally by rotating the spool such that one ligation band is applied to the tissue as the corresponding beads on each single filament are withdrawn into the working channel of the endoscope.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Figure 1:
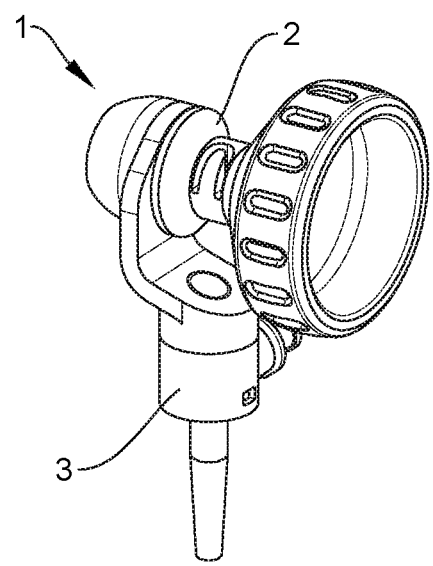
FIG. 1 shows an embodiment of a mechanical device.

In general, a mechanical device for coupling to an access device, such as an endoscope, is provided. The mechanical device can be provided as an add-on kit for attachment to an endoscope or other access device just prior to or during surgery, and the mechanical device can be configured to apply one or more ligation bands to tissue to be ligated. FIG. 1 illustrates one exemplary embodiment of a mechanical device 1 (see FIG. 1) that can be inserted into the accessory port of an endoscope. As shown, the mechanical device 1 includes a control handle for conducting a multi-band ligation procedure.

Figure 2:
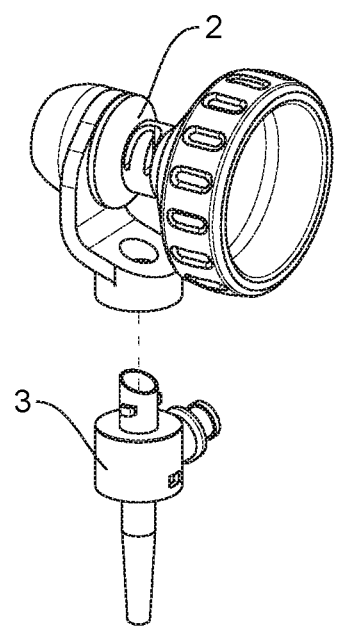
FIG. 2 shows an embodiment of a mechanical device.
Figure 3:
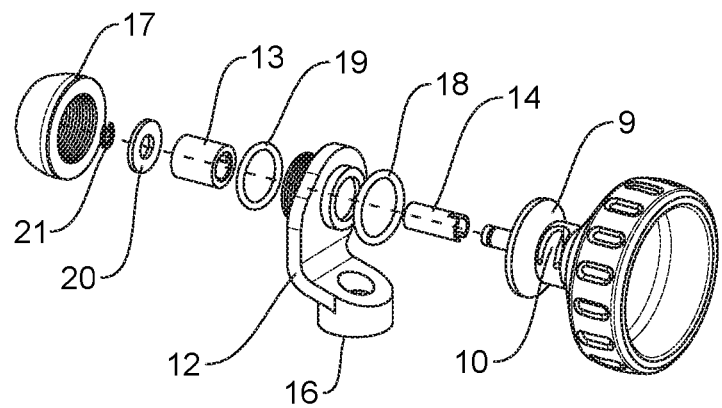
FIG. 3 shows an exploded view of an embodiment of a rotating spool assembly.
Figure 6:
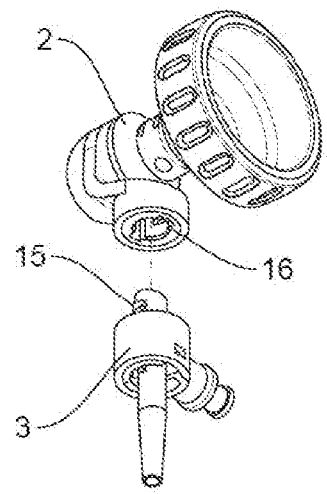
FIG. 6 shows an embodiment of a mechanical device.

In one embodiment, the mechanical device includes a rotating spool assembly 2 and a disposable valve assembly 3 (see FIGS. 1-3). The rotating spool assembly 2 can be configured to be a re-usable element, wherein the components can be formed from specific materials (such as surgical grade stainless steel, titanium, or other metals) and assembled in such a way to enable sterilization and use with a plurality of patients. The disposable valve assembly 3 can include a mating stem member 4 (with an upper body 7), a sealing member 5, a flushing port member 6, and a tip 11. The upper body 7 of the mating stem member 4 includes tabs 15 (see FIG. 6). These elements are combined into an assembly that can be formed as a single disposable entity. The flushing port member 6 may have a luer taper, allowing fluid fittings to make leak-free connections between mating taper-fitting-parts.

The means through which the disposable valve assembly 3 and rotating spool assembly 2 are attached can allow for rapid assembly and disassembly. In an exemplary embodiment, attachment can be achieved via insertion and rotation of the disposable valve assembly 3 into the rotating spool assembly 2, for example using a quarter turn bayonet fitting (see FIGS. 2 and 6).

The disposable valve assembly 3 and the rotating spool assembly 2 may also be rigidly attached to each other through mechanical means so that the disposable valve assembly 3 and rotating spool assembly 2 are treated as a single entity and disposed of after single patient use (see FIG. 1).

Figure 4:
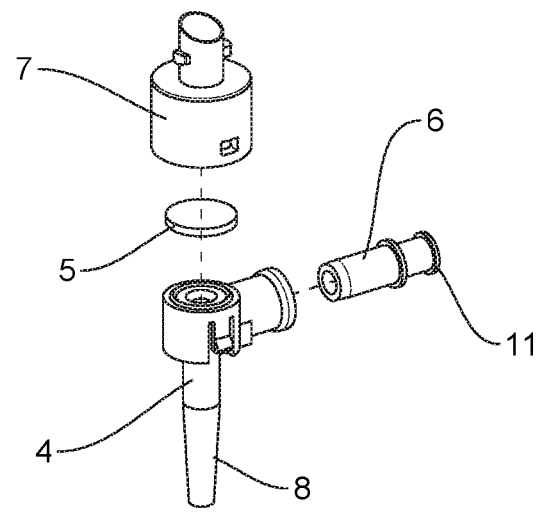
FIG. 4 shows an exploded view of an embodiment of a disposable valve assembly.

Also provided herein is a mating stem member 4, as illustrated in FIG. 4. The mating stem member 4 can be shaped to mate with an endoscope accessory port. For example, a taper on the insertion stem 8 can be provided to allow the tapered geometry to form a surface-to-surface mate with the internal geometry of an endoscope accessory port 601, upon insertion to an endoscope 600 (see FIG. 5). The elongated portion above the tapered portion can also be engineered to be long enough so that it accommodates the height of all endoscopic caps currently on the market without detriment to the surface-to-surface mate with the internal geometry.

The rotating spool assembly 2 can include a hub 16 with an arm 12. This enables the easy removal of the release cord 201 by counter-clockwise unravelling along the axis of the rotating spool 9 and provides an open design to increase access to the rotating spool assembly 2 (see FIGS. 1, 3, and 17).

In an exemplary embodiment, the rotating spool assembly 2 features a hooking member 10 on the central rotating section of the spool 9. This hooking member 10 can mate to the loop member 209 of the release cord 201 of the multi-band ligation device and is an exemplary embodiment of the functionality which allows a multitude of different coupling methods to be utilized, if so desired (see FIGS. 2, 3, and 17). The spool 9 can be rotated to draw the release cord 201 up through the working channel of the endoscope and wrap around the spool 9. The rotating spool assembly 2 can also include an end cap 17, a circlet 21, a washer 20, a clutch 13, O-rings 19, 18, a cylinder 14, and a receiver 16 (see FIGS. 3 and 6).

Figure 7:
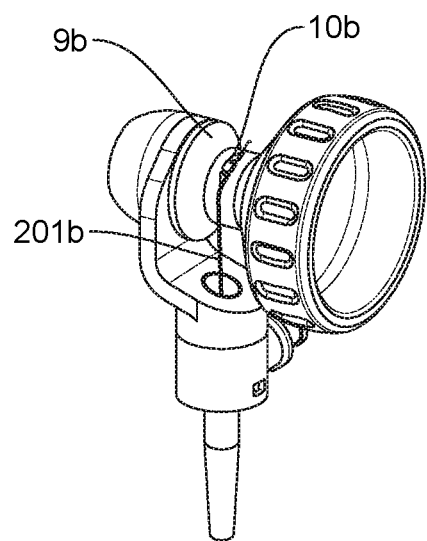
FIGS. 7-9 show embodiments of a mechanical device with a spool.

An alternate embodiment for attaching the release cord 201b to the spool 9b is for the spool 9b to incorporate a tapered toothed groove 10b such that, on drawing the release cord 201b into the groove, it is gripped and held securely (see FIG. 7).

Figure 8:
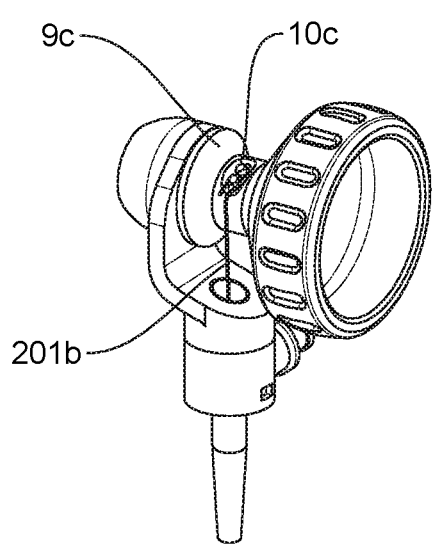

Another embodiment for attaching the release cord 201b to the spool 9c is for the spool 9c to incorporate two or more posts 10c such that wrapping the release cord around said posts 10c in a figure of eight causes the release cord 201b to be held by friction (see FIG. 8).

Figure 9:
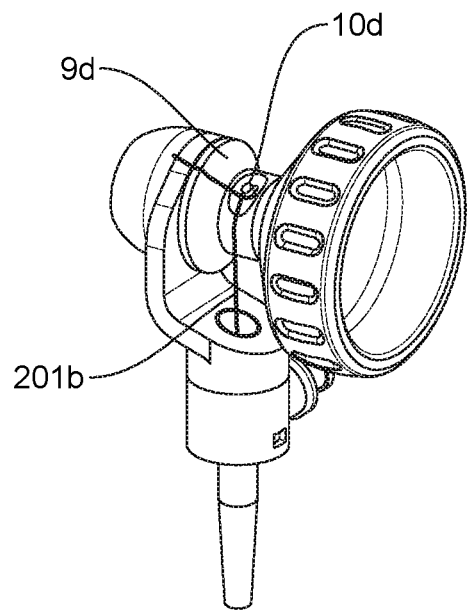

Another embodiment for attaching the release cord 201b to the spool 9d is for the spool 9d to incorporate a single post 10d and the spool 9d a slot such that wrapping the cord 201b around the post 10d aligns the cord 201b and fitting the cord into the spool 9d slot retains the cord 201b (see FIG. 9).

An accessory or instrument is also provided to be used in conjunction with a multi-band ligation device 1. This accessory is presently provided as a loading wire 101 that facilities the loading of the ligation band release cord, from the distal end of the working channel of a flexible endoscope to the proximal end of the working channel, until it exits through the accessory port of said endoscope, at which point the release cord may couple with the rotating spool of a multi-band ligation device handle (see FIG. 10). The loading wire 101 may be passed down the working channel from the accessory port to the distal end of the endoscope. The release cord 201 can be hooked on the loading wire 101, at which point the loading wire 101 can be withdrawn up the working channel. The release cord 201 can then be drawn up the working channel from the distal end to the proximal end attached to the loading wire.

The simplicity of construction and manufacture of the loading wire 101 can be beneficial to the user. The loading wire 101 may be formed from a single piece of metallic wire that is post-formed to give it added functionally and improvements not seen in any similar devices.

Figure 10:
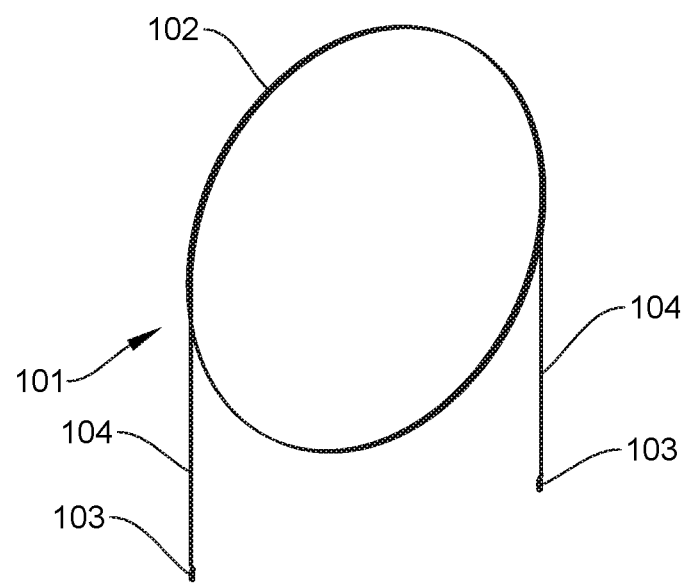
FIGS. 10-16 show embodiments of an accessory.
Figure 11:
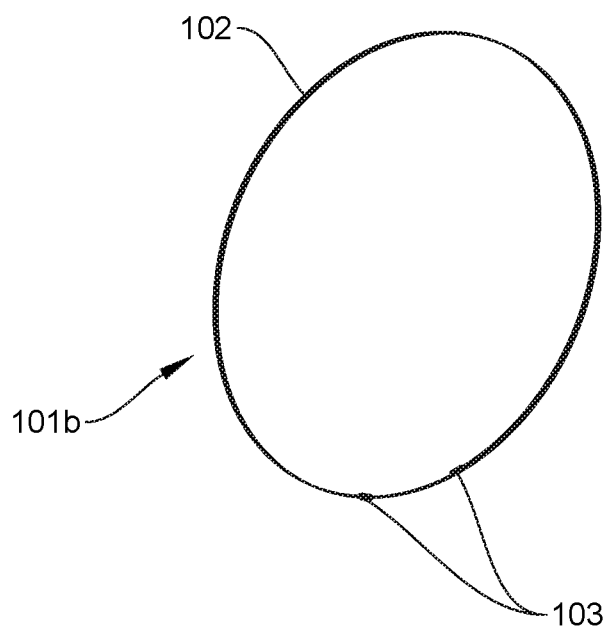

One advantage is the coiled configuration 102 of the wire (see FIGS. 10-11). The metallic wire is post formed into a coiled shape 102 which adds benefits in terms of ease of handling and control for the operator. Because of the functionally of traveling through the working channel of endoscopes, the loading wire 101 needs to be very long, which can make handling and control of the loading wire 101 very difficult for the operator. By its very nature a coiled configuration 102 is much easier to handle and control and makes the process more manageable for the operator. Once the loading wire 101 is inserted into the endoscope working channel the coiled configuration 102 no longer becomes an issue as the loading wire 101 takes the shape of the working channel. On removal the loading wire 101 then returns to its coiled configuration 102, and this can present several safety benefits for the user. For example, the coiled configuration can prevent the wire from jumping into the visual field of the user and/or assistant. The coiled configuration is also less likely to contact the floor or other unclean surfaces during the loading process. Finally, if the loading wire is put down onto the small accessory tables and is needed to re-load the device for more band placements, it is much more likely to remain in place in a tight coil on the small accessory stand.

In an exemplary embodiment, the loading wire 101 incorporates straight sections 104 at the ends of the wire, to enable ease of entry into the endoscope working channel (see FIG. 10). Alternately the loading wire 101b could be formed as a complete coiled component without straight ends (see FIG. 11).

Figure 12:
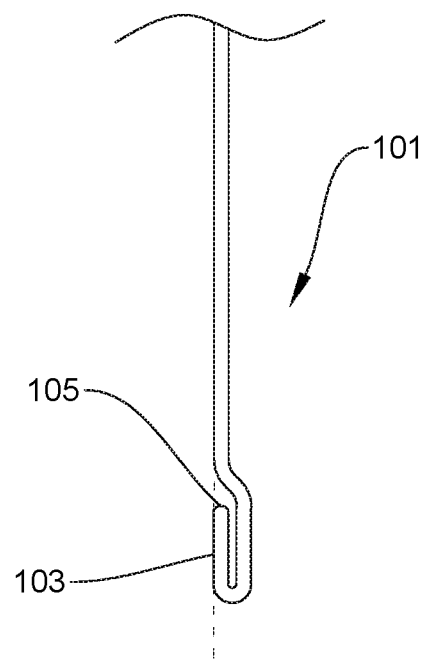
Figure 13:
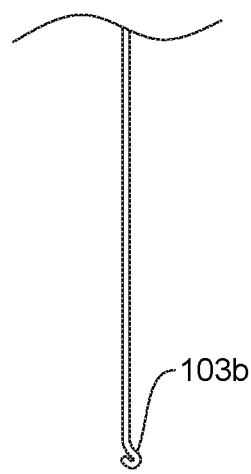
Figure 14:
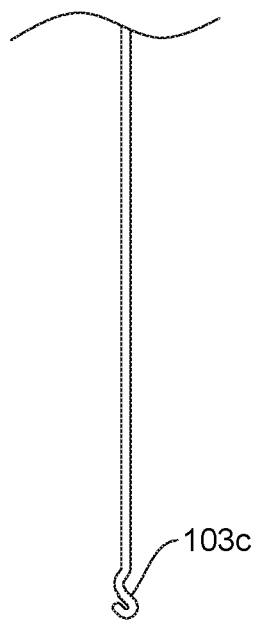
Figure 15:
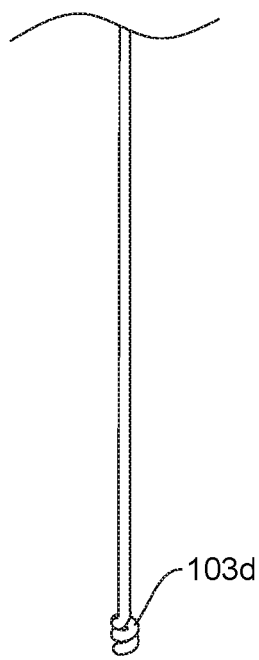
Figure 16:
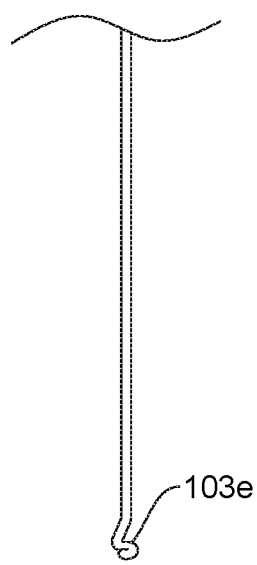

A hook-like configuration 103 can be integrated on either or both ends of the loading wire 101 (see FIG. 12). The hook-like configuration 103 can be formed from the same single piece of wire, meaning any possibility of detachment of the hook component 103 is removed, which greatly adds to user confidence and increases patient safety. The hook-like configuration 103 can also be shaped to ensure that the possibility of the hook 103 catching on or snagging and damaging other medical equipment is drastically reduced given its low-profile design. The ends may also be formed into additional configurations (see FIGS. 13-16).

There is also a secondary accessory or instrument to be used in conjunction with a multi-band ligation device 1. The accessory is presently defined as a release cord 201 which facilitates the release of elastic ligation bands (see FIG. 17). The release cord 201 travels from the distal end of the working channel of a flexible endoscope to the proximal end of the working channel, until it exits through the accessory port of said endoscope at which point the release cord 201 may couple with the rotating spool 9 of a multi-band ligation device handle.

Figure 17:
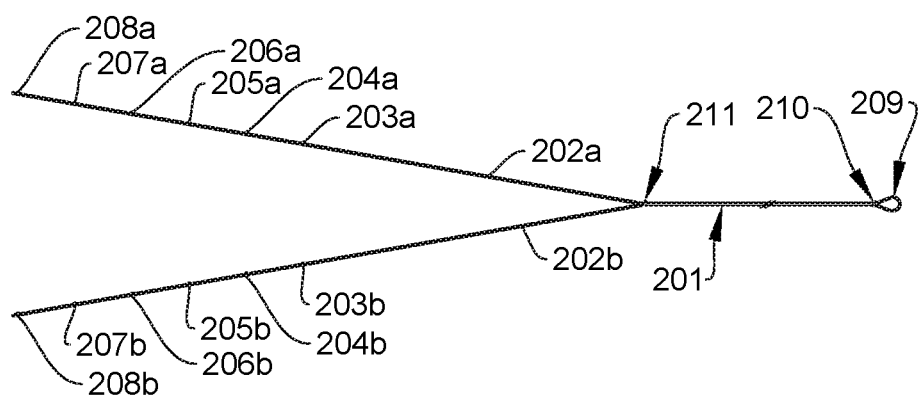
FIGS. 17-21 show embodiments of a second accessory.
Figure 18:
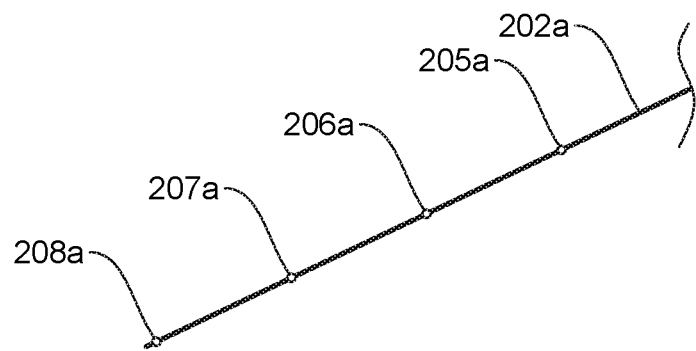
Figure 19:
Figure 20:
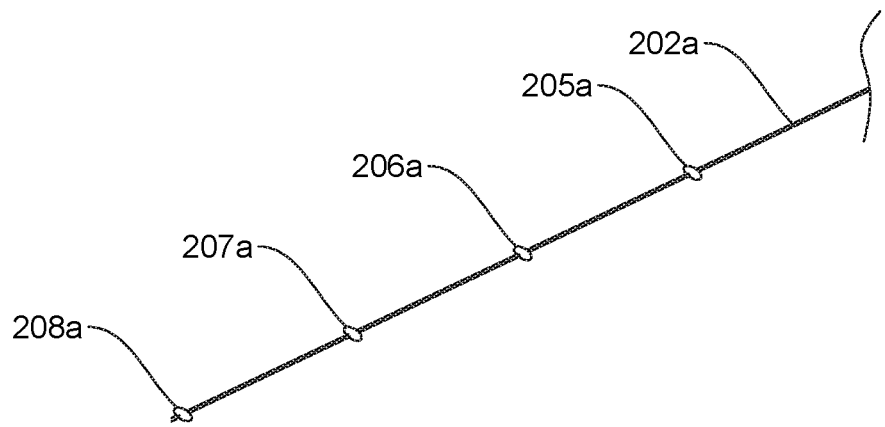
Figure 21:
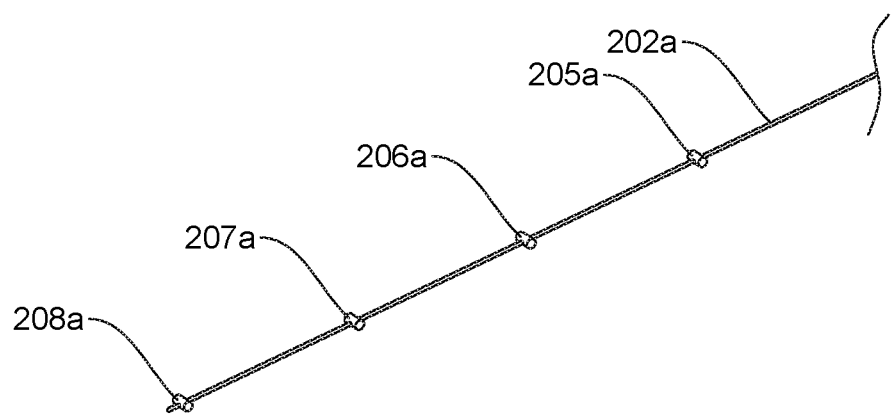

The cord can also include beads 203-208 positioned in pairs, with one bead 203-208 on each filament 202, spaced at set intervals along the length of the single filament 202 (see FIGS. 17-18). The pairs of beads 203-208 can be configured in a staggered and offset configuration, so the beads 203-208 are not positioned side-by-side (see FIG. 19). This means that, when the beads 203-208 are pulled inside the working channel, no two beads 203-208 will be side by side and occlude the working channel of the endoscope. The fact they are offset and staggered can reduce the possibility of the working channel becoming occluded. The more space that is available in the accessory channel during or after banding will increase the options for devices placed subsequently. Variously shaped beads may also be used (see FIGS. 20-21).

Figure 5:
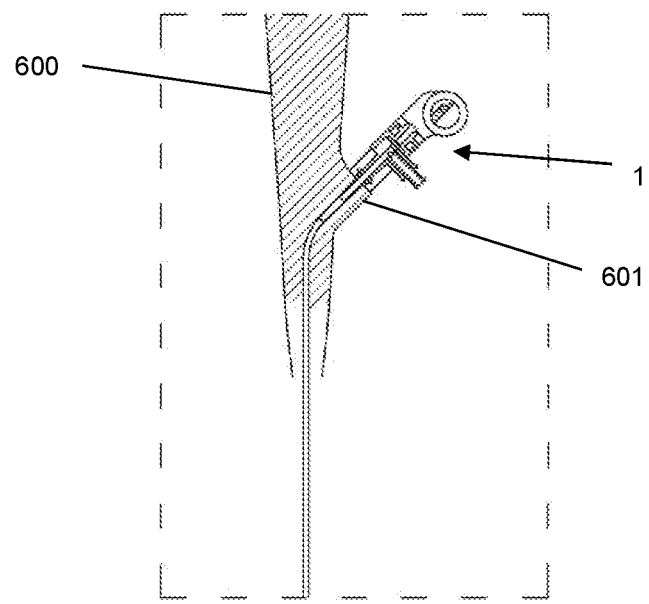
FIG. 5 shows an embodiment of a mechanical device in operation with an endoscope.
Figure 23:
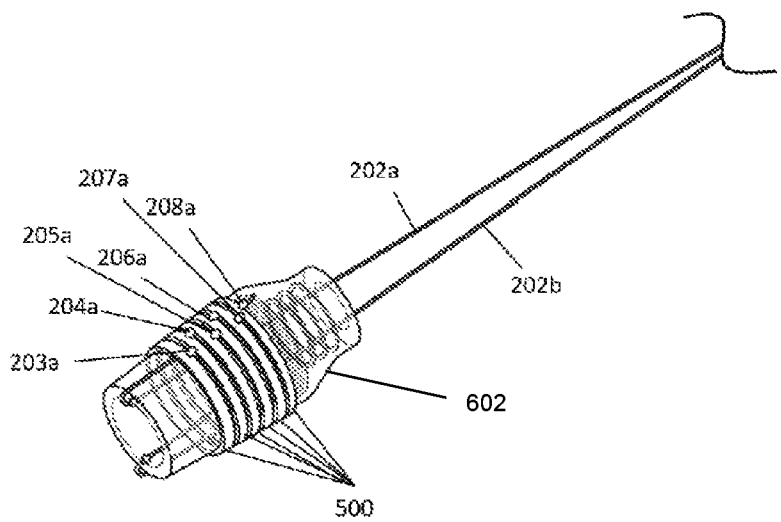
FIGS. 23-24 show examples of multi-band ligation devices.
Figure 24:
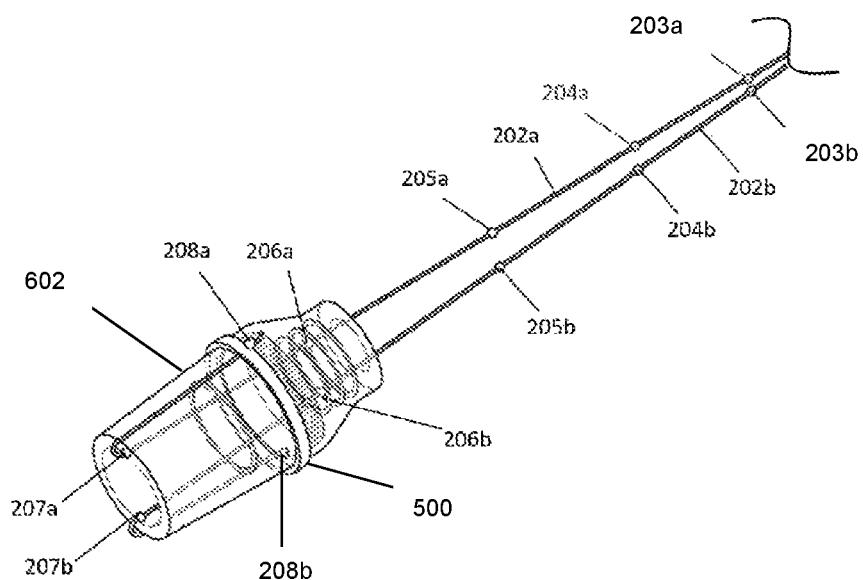

Ligation bands 50Q illustrated in FIGS. 23 and 24, can be placed around an outside distal end 602 of an endoscope, such as endoscope 600 illustrated in FIG. 5, in front of sets of the beads 203a, 203b-208a, 208b. The release cord 201 can be withdrawn up the working channel of the endoscope, which can cause the beads 203a, 203b-208a, 208b to be withdrawn around the distal end 602 of the endoscope 600. The ligation bands 500 can be caused by the beads 203a, 203b-208a, 208b to be pushed distally off of the distal end 602 of the endoscope 600, thereby applying the band to the tissue drawn into the endoscope 600.

Figure 22:
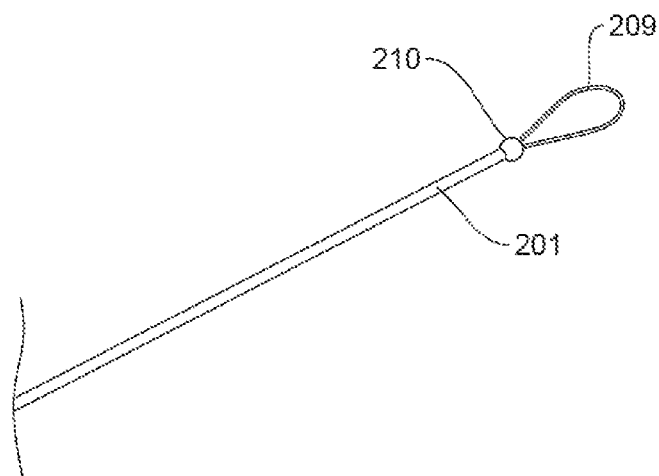
FIG. 22 shows an embodiment of a release cord.

In one embodiment, there is a looped nature 209 to the proximal end of the release cord 201 (see FIGS. 17 and 22). Having a closed loop configuration 209 at the proximal end of the cord 201 allows for a variety of attachment methods to any number of coupling modalities. It also ensures that these couplings will be safe and secure, which adds to operator confidence and results in better outcomes for patients through faster and more efficient procedures. These are procedures that are done in high stress conditions and in units where the light is usually very low in order to read the monitors involved.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic surgical device, comprising:
   a rotating spool assembly having a hub, an arm contiguous with the hub, and a rotating spool inserted through the arm, the hub having an opening formed therein;
   a valve assembly having a mating stem member, a sealing member, and a flushing port member, the mating stem member having a lumen extending through a longitudinal center thereof and having the sealing member extending thereacross, the lumen being aligned on a proximal end of the mating stem member with the opening in the rotating spool assembly, and the valve assembly being coupled to a distal end of the rotating spool assembly; and
   a braided cord having first and second single filaments, the first and second single filaments being braided together at a proximal end of the braided cord and separated at a distal end of the braided cord, the proximal end of the braided cord being configured to attach to the rotating spool, the distal end of the braided cord being configured to pass through the lumen of the mating stem member, a plurality of beads being formed along a length of each of the first and second single filaments at the distal end of the braided cord, the plurality of beads being positioned such that no two beads are at a same distance from the proximal end of the braided cord and the plurality of beads are offset from one another when the braided cord is pulled proximally through the lumen.

2. The device of claim 1, wherein the rotating spool assembly includes a substantially hook-shaped member that rotates as one with the spool, the substantially hook-shaped member being configured to receive a cable.

3. The device of claim 1, wherein the spool comprises a tapered toothed groove sized to grip a release cord.

4. The device of claim 1, wherein the spool includes first and second posts protruding from a surface thereof and positioned next to one another, the first and second posts being configured to receive a cable therearound.

5. The device of claim 1, wherein the spool comprises at least one post protruding from a surface thereof and a groove in the surface positioned proximally from the post.

6. The device of claim 1, wherein the mating stem member includes an upper body with one or more tabs formed on the upper body.

7. The device of claim 1, wherein the mating stem member includes a tapered section at a distal end thereof, and the tapered section is shaped to be inserted into an auxiliary port of an endoscope to form a surface-to-surface mating engagement with a corresponding internal geometry of the auxiliary port.

8. The device of claim 1, wherein the rotating spool assembly couples to the valve assembly using a quarter turn bayonet fitting.

9. An endoscopic surgical device, comprising:
a spool assembly having a rotating member and a stem having a lumen extending therethrough;
a release cord having first and second strands, the first and second strands being engaged with one another at a proximal end of the release cord and separated at a distal end of the release cord, the proximal end of the release cord being configured to attach to the rotating member, the distal end of the release cord being configured to pass through the lumen of the stem and a lumen of an endoscope, a first plurality of beads positioned along, a length of the first strand, a second plurality of beads positioned along a length of the second strand, a position of each of the first plurality of beads on the first strand being staggered from a position of each of the second plurality of beads on the second strand such that none of the first and second plurality of beads contact one another when the first and second strands are drawn proximally through the lumen of the endoscope; and
a loading wire extending through the lumen in the stem of the spool assembly and having a proximal end extending proximally from the lumen in the stem and having a distal end extending distally from the lumen in the stem, the distal end having a hook formed thereon and configured to couple to a thread such that the proximal end of the loading wire can be pulled proximally to pull the thread through the spool assembly, the hook being formed from the wire being turned back upon itself, and a central axis of a distal-most end of the wire forming the hook being co-linear with a central axis of a proximal portion of the wire.

10. The endoscopic surgical device of claim 9, wherein the loading wire is formed from metal drawn out into a thin flexible thread.

11. The endoscopic surgical device of claim 9, wherein the loading wire is formed from a braiding of two or more single wires.

12. The endoscopic surgical device of claim 9, wherein the loading wire is formed from a polymer.

13. The endoscopic surgical device of claim 9, wherein a central segment of the loading wire forms one or more coils, and proximal and distal portions of the wire are at least partially formed of straight sections.

14. A release cord comprising:
a braided cord having first and second single filaments, the single filaments being braided together at a proximal end of the braided cord and separated at a distal end of the braided cord, the braided cord being configured to extend through an endoscope; and
a plurality of beads formed along a length of each of the first and second single filaments at the distal end of the braided cord, wherein the plurality of beads are positioned such that no two beads on either of the first and second filaments are at a same distance from the proximal end of the braided cord and the plurality of beads are all staggered when the braided cord is withdrawn proximally through the endoscope.

15. The release cord of claim 14, wherein the beads are substantially spherical.

16. The release cord of claim 14, wherein the beads are made of a polymer.

17. The release cord of claim 14, wherein a proximal section of the release cord is formed into a closed loop configuration, and the closed looped configuration is sized to fit through a working channel of an endoscope.

18. The release cord of claim 14, wherein the closed looped configuration at the proximal end is created by attaching a separate closed loop shaped component through mechanical means.

19. A system for tissue ligation comprising:
a rotating spool assembly having a hub and a spool, an opening being formed in the hub;
a valve assembly having a mating stem member, a lumen extending through a longitudinal center of the mating stem member and aligned on a proximal end of the mating stem member with the opening in the rotating spool assembly, the valve assembly being coupled to a distal end of the rotating spool assembly;
a wire having a cross sectional dimension not exceeding the lumen of the valve assembly, and hooks being formed on each end of the wire; and
a release cord having a braided cord with first and second single filaments, the first and second single filaments being braided together at a proximal end of the braided cord and separated at a distal end of the braided cord, a plurality of beads being formed along a length of each of the first and second single filaments at the distal end of the braided cord, each bead of the plurality of beads along the first single filament being at a different distance along the first single filament relative to the proximal end of the braided cord than any bead of the plurality of beads along the second single filament relative to the proximal end such that each bead of the plurality of beads is offset from each other bead when the release cord is retracted proximally through an endoscope.

20. The system of claim 19, wherein the spool comprises a substantially hook-shaped member on a surface thereof, and the proximal end of the braided cord is attached to the substantially hook-shaped member.

21. A method for assisting with tissue ligation, comprising:
passing a loading member having a wire with a hook formed on at least a distal end through an opening in a rotating spool assembly having a spool, distally along a lumen formed in a valve assembly coupled to the rotating spool assembly, and distally along a length of a working channel of an endoscope such that the hook protrudes from a distal end of the working channel, the hook being formed from the wire being turned back upon itself, and a central axis of a distal-most end of the wire forming the hook being co-linear with a central axis of a proximal portion of the wire;
securing a proximal end of a release cord onto the hook, the release cord having a braided cord with at least two single filaments, the single filaments being separated at a distal end of the braided cord and having a plurality of beads formed along a distal length of each of the single filaments in a staggered arrangement;
drawing the proximal end of the release cord proximally through the working channel, the valve assembly, and the rotating spool assembly until the proximal end of the release cord protrudes from a proximal end of the rotating spool assembly, the staggered arrangement of the plurality of beads preventing any, of the plurality of beads from contacting one another when the single filaments and the plurality of beads are drawn through the working channel; and attaching the proximal end of the release cord to the spool of the rotating spool assembly.

22. The method of claim 21, wherein the plurality of beads on the single filaments of the release cord are positioned such that no two beads are at a same distance from the proximal end of the braided cord.

23. The method of claim 21, further comprising wrapping a plurality of ligation bands around an outside distal surface of the endoscope, each ligation band being positioned in front of corresponding sets of beads on each of the single filaments.

24. The method of claim 23, further comprising positioning a distal end of the endoscope against a tissue to be ligated, and retracting the release cord proximally by rotating the spool such that one ligation band of the plurality of ligation bands is applied to the tissue as the corresponding beads on each single filament are withdrawn into the working channel of the endoscope in the staggered arrangement.

* * * * *